United States Patent
Honkura et al.

(10) Patent No.: US 6,203,325 B1
(45) Date of Patent: Mar. 20, 2001

(54) DENTAL MAGNETIC ATTACHMENT AND ITS FIXING METHOD INCLUDING SPACER

(75) Inventors: Yoshinobu Honkura; Kazuo Arai; Kazunari Kimura, all of Tokai (JP)

(73) Assignee: Aichi Steel Works, Ltd., Tokai (JP)

(*) Notice: Subject to any disclaimer, the term of this patent is extended or adjusted under 35 U.S.C. 154(b) by 0 days.

(21) Appl. No.: 09/381,977

(22) PCT Filed: Oct. 16, 1998

(86) PCT No.: PCT/JP98/04700

§ 371 Date: Oct. 5, 1999

§ 102(e) Date: Oct. 5, 1999

(87) PCT Pub. No.: WO99/39656

PCT Pub. Date: Aug. 12, 1999

(30) Foreign Application Priority Data

Feb. 5, 1998 (JP) ................................. 10-024533

(51) Int. Cl.[7] .................. A61C 13/12; A61C 13/225; A61C 13/235
(52) U.S. Cl. ............................ 433/177; 433/189
(58) Field of Search .................... 433/172, 177, 433/189

(56) References Cited

U.S. PATENT DOCUMENTS

| 4,626,213 | 12/1986 | Shiner et al. |
|---|---|---|
| 4,815,975 | * 3/1989 | Garell et al. ............... 433/189 |
| 4,957,438 | * 9/1990 | Bax ............................ 433/189 X |
| 4,993,950 | * 2/1991 | Mensor, Jr. ................ 433/189 X |
| 5,417,570 | * 5/1995 | Zuest et al. ................. 433/177 |
| 5,871,357 | * 2/1999 | Tseng ......................... 433/189 |

FOREIGN PATENT DOCUMENTS

| 7-246208 | 9/1995 | (JP) . |
|---|---|---|
| 8-266557 | 10/1996 | (JP) . |
| 9-154856 | 6/1997 | (JP) . |
| 10-127662 | 5/1998 | (JP) . |

* cited by examiner

*Primary Examiner*—Nicholas D. Lucchesi
(74) *Attorney, Agent, or Firm*—Jacobson, Price, Holman & Stern, PLLC

(57) ABSTRACT

A dental magnetic attachment having good cushioning properties against a compressing pressure which makes a denture sink appropriately on biting. The dental magnetic attachment embedded in the denture base for holding the denture in the oral cavity by a magnetic attractive force working with the magnetic assembly and a soft magnetic keeper embedded in the top of the root surface includes a magnetic assembly and a cap covering the top of the magnetic assembly. The magnetic assembly has a hollow in the center of its top. The cap with a button is placed on the magnetic assembly, inserting the button into the hollow to contact to its bottom. On biting, the button is compressed, to be deformed with a shorter thickness and at this time a sleeve formed as a body around the core slides down along the side of the magnetic assembly to reduce the thickness of the dental magnetic attachment. This sliding makes the denture sink uniformly and appropriately. The dental magnetic attachment has good cushioning properties and offers a good feeling to a patient when biting with the denture.

15 Claims, 13 Drawing Sheets on non loading gap — 11, 21, 22, 223, 221, 2, 224, 222, 32, 3, 12 gingiva(F) — 31, 210, T, F on loading 11, 21, 22, load, 223, 2, 32, 3, 12 gingiva(F)shrinking makes the denture sink — 31, 210, T, F on non loading on loading

DENTAL MAGNETIC ATTACHMENT AND ITS FIXING METHOD INCLUDING SPACER

TECHNICAL FIELD OF THE INVENTION

The present invention relates to a dental magnetic attachment which is embedded in a denture to stabilize the denture on abutment teeth in the oral cavity using magnetic attractive force.

DESCRIPTION OF THE PRIOR ART

Up to the present, a dental magnetic attachment which strongly stabilize the denture on abutment teeth by magnetic attractive force is well known. Its force is acted between a magnetic assembly in a denture and a keeper made from a soft magnetic material embedded in a root cap.

However conventional types of dental magnetic attachment have a week point to give damage to an abutment tooth with a keeper when they are applied to dentures. Each biting makes nearly equal pressure to any artificial teeth of the denture. In the case of free saddle denture shown as FIG. 22, the parts on the abutment tooth marked as A shows only small sinking depth of about 0.02 mm, on the other hand the parts on gingiva marked as B shows large scale sinking depth of about 0.2 mm. It means that the sinking depth of the part B is ten times larger than that of the part A. This difference about sinking depth between the part A and the part B concentrates the biting force on the abutment teeth. This concentration is apt to injure the abutment teeth. In some cases the difference makes denture to be leaned so that the denture is put out of the place.

For solving this problem, Japanese Patent application Laid Open(KOKAI) No.7-246208 discloses a cushioned type of dental magnetic attachments shown in FIG. 23. That has a cap made of an elastic material which is attached to the top of the magnetic assembly by self curing adhesive. U.S. patent application Ser. No. 4,626,213 discloses another cushioned type of dental magnetic attachments shown in FIG. 24. That also has a cap made of an plastic material which covers the magnetic assembly with a circular side.

The former patent describes that the magnetic attachment has a cushion ability to relief a biting force which is loaded to the denture by means of the elasticity of the cap. But shrinking of the cap toward the vertical direction is accompanied by extention of the cap toward the traverse direction due to the elastic property of the cap material which is expressed by the constant of Poisson ratio. Therefore when it is designed to get the considerably large shrinking, it must have large extension. This large extension makes large stress or gap between the side of the magnetic assembly and its periphery. This gap is apt to cause some trouble that something such as dregs of food is put into the gap and is rotten in it. This elastic motion makes separation or some gap between the magnetic assembly and the cap which are attached by self curing adhesive.

On the contrary when the cap of this type is designed to make the traverse extension to be small, vertical shrinking inevitably comes to be small. In the case, enough vertical shrinking for practical use is not obtained. That is, there remains the large difference of sinking depth between the parts on the abutment teeth and the parts on gingiva, which makes the denture to be inclined and sometimes to be put out of the place.

The latter patent describes that the magnetic attachment has a rotary ability which is given by the seesaw motion of the cap on the magnetic assembly. This motion is made by sliding the cap along the circular side of the magnetic assembly. The seesaw motion can solve the problem that denture is put out of the place due to leaning the denture But it does not show an enough cushion ability to the vertical pressure caused by biting force. Because its mechanics can make only small vertical motion between the magnetic assembly and the cap. When biting, the pressure is concentrated on the abutment teeth to injure them. So it is concluded that this type gives not enough solution on the drawback of conventional types of magnetic attachment, especially when it is applied to free saddle denture.

THE PROBLEMS TO BE SOLVED BY THE INVENTION

The first object of the invention is to provide a dental magnetic attachment which has a cushion cap for protecting the abutment toeth from harmful biting force and for keeping the denture firmly on the abutment teeth to be free from shaking or leaning. This cap makes enough sinking depth on biting so that there is no concentrration of the biting force on the abutment teeth. It is resulted that the denture is free from leaning so as to be kept firmly on the keeper embedded into the root cap. Moreover it is necessary that this cap is kept as a body with the magnetic assembly.

The second object of the invention is to offer the method and instrument for fixing the magnetic assembly with the above mentioned cushion cap to the denture.

When the vertical pressure is loaded on the magnetic attachment, he cap placed on the top of the magnetic assembly can slide along the side of the magnetic assembly in the vertical direction. If the maximum of the biting force is loaded, the cap can sink about 0.20 mm until the front of the sleeve reaches to the bottom surface of the magnetic assembly which is magnetically attached to the top surface of the keeper. If not loaded, the cap is placed on the beginning position. The mechanics which can slide the cap about 0.20 mm, needs a space of 0.20 mm in height around the magnetic assembly.

The magnetic assembly with the cap is used to be embedd into the denture. As for the setting method, first it is placed in the hollow of the denture base made of resin and next is fixed by self curing adhesive. Here since controlling the volume of the adhesive at the optimum is difficult, it is popular that much volume of the resin more than necessity is used. If the volume of resin is less than necessity, enough adhesive strength can not be got. In this case, we would meet with a big problem that the magnetic assembly will drop out of the denture.

From above reason, much resin more than necessity is used when the magnetic assembly is set. As there is the space around the magnetic assembly for sliding, the excess of the self curing adhesive is apt to fill up the space. It means that the space for sliding decreases or disappeares.

The present invention offers the method how to fix the magnetic assembly with the cushion cap to the denture together with a spacer to keep the above mentioned space.

SUMMARY OF THE INVENTION

A dental magnetic attachment disclosed by the present invention is united with a magnetic assembly and a cushion cap. The dental magnetic attachment which is embedded into the denture retains the denture on the abutment teeth by the magnetic force acting between the magnetic assembly and the keeper placed on the teeth root. The characteristic of the present attachment is that the magnetic assembly is covered with a cap made of elastic material and the cap can slide in the vertical direction along the side of the magnetic assembly. The cap is designed to hp united with a core and a sleeve. The core is placed at the designated distance of about 0.20 mm over the top of the magnetic assembly. When the biting force is loaded, the core is dislocated until touching to the top of the magnetic assembly. The sleeve formed around the core can slide down from the beginning position to the bottom of magnetic assembly on loading. However the sleeve is tightly fit to the magnetic assembly so as not to take off.

The present attachment with the cushion cap has capability to sink until the core would touch to the top of the magnetic assembly due to the biting force on biting. Applying the present attachment to the denture, the cushion mechanics can make sinking at the parts on the abutment teeth as much as that at the parts on the gingiva when biting. Uniformly sinking is related that the denture is supported by the abutment teeth and the gingiva impartially. In other words the biting force on the denture is dispersed to gingiva in stead of concentrating on the abutment teeth, so that the abutment teeth is protected from too large biting force. This cushion mechanics also makes the seesaw motion of the cap on the contact point with the button of the cap and the top of the magnetic assembly as a fulcrum by sliding the sleeve along both left and right sides of the magnetic assembly in the opposite direction each other when biting.

The seesaw motion makes the denture not to lean on the abutment teeth and prevent the magnetic attachment from lifting up over the keeper. From this mechanics, the denture is kept firmly on the gingiva. Moreover when the cap moves on each biting, the core of the cap is deformed, but the sleeve is not only sliding but also holding the cap tightly fit to the side of the magnetic assembly without deformation. The tight contact with them keeps the cap to be not removed from the magnetic assembly on each biting.

A preferable structure of the present magnetic attachment is composed of a magnetic assembly which has a hollow on the center of the top surface and a cap which has a button on the inner surface of the core of the cap made of the elastic material, where the button is inserted in contact with the bottom of the hollow. The button offers better cushion property to the present magnetic attachment, because it can be elastically compressed more than the core. The pressure on biting is concentrated to this button, so that it shows large elastic deformation in the hollow. In other words, the superior cushion property is obtained by making a proper design of the button which is made to determin what kind of the elastic material and how size of a button dimension.

Other merit of this preferable one is that the maximum deformation of the button which corresponds to the sinking depth or sliding distance of the cap against the magnetic assembly is restricted by the top surface of the magnetic assembly. The button cannot deform after reaching to the top surface of the magnetic assembly. Therefore the maximum deformation is controlled by the gap between the inner surface of the core and the top surface of the magnetic assembly on non-loading. The recommendable design aboout the gap is that the maximum deformation of the button induced by maximum pressure in biting is equal to the gap. This good designated gap is useful to prevent the cap from deforming too much in loading more than expectation. If not, the cap is damaged by too much deformation and self curing adhesive pasted with the cap and the denture base is broken.

(The method for fixing to the denture)

As for the method for fixing the present magnetic attachment to the denture, conventional method widely used in the dental field is done mostly according to that the attacnment is put on the keeper in the teeth root, then inserted into the hollow of the denture and after that it is fixed to it by self curing adhesive. But it is necessary for getting the cushion property to keep the space under the sleeve around the magnetic assembly. For keeping the space, a spacer used in the present attachment has an inner diameter same to the outer diameter of the magnetic assembly and it is inserted into around the magnetic assembly to be set under the front of the sleeve of the cap. The magnetic attachment united together with thee magnetic assembly ad the spacer is inserted into the hollow of the denture, then is fixed by self curing adhesive which cannot enter the space because of the spacer, and after that the spacer is removed to make the space for sliding. Briefly speaking, this fixing method is characterized by using the spacer.

In the present method as above mentioned, the spacer prevents the excess of self curing adhesive existing in the gap between the cap and the denture's hollow from entering the space when the magnetic attachment is put into the hollow of the denture. The self curing adhesive cannot enter the space because the space under the front of the sleeve around the magnetic assembly is filled up by the spacer. When the spacer is removed from the denture after curing, there remains the space to make it possible to slide the cap along the side of the magnetic assembly even if there exists too much excess of the adhesive in the gap.

Therefore the present method makes advantage that the magnetic attachment can be firmly fixed to the denture with easy and without fail. It also is possible that the space to be necessary for sinking the denture can be kept without taking too much care in the fixing procedure.

There are other methods to make it possible to disappear the spacer. For example, there is a chemical method to dissolved it by saliva. But the recommendable method is to remove the spacer mechanically after curing. This mechanical removing after curing offers some advantages to be done in a moment and kept enough space for the denture to sink as much as designed.

(The spacer for fixing to the denture)

The spacer is used temporally for fixing the present magnetic attachment to the denture. The magnetic attachment consists of the magnetic assembly retained to the keeper on the abutment teeth by the magnetic force and the cap covers the top of the magnetic assembly to make sliding along the side of the magnetic assembly. The magnetic attachment with the spacer to be set at the position under the front of the sleeve of the cap is put in the hollow of the denture where self curing adhesive is filled partially. After the magnetic attachment is fixed to the denture by curing, the spacer is removed to make the space around the magnetic assembly. Through the above procedure, the spacer can offer the function to prevent the adhesive from entering the space. Even if there is much excess of the adhesive, the space is kept by the spacer.

A ring shaped spacer is preferable or recommendable because the magnetic assembly and the cap are generally cylindrical in shape. The magnetic attachment is fixed to the denture in a body with the spacer which is attached to the outer side of the magnetic assembly at the position under the front of the sleeve. If all of the magnetic assembly, the cap and the spacer are axis symmetrical in shape, it is easy to assemble them into one with a high accuracy. It means that there is only a little gap between the front of sleeve and the top of the spacer, as well as almost no gap between the outer side of the disk shaped magnetic assembly and the inner side of the ring shaped spacer. It is natural that the too narrow gap makes it impossble for the adhesive to enter into the space. In other words, the spacer assures to make the space without fail. As a result, the space equalto the thickness of the spacer is made around the magnetic assembly when the spacer is removed after curing. This space makes it possible to slide down the sleeve of the cap along the outer side of the magnetic assembly. In the case that the denture may be pressed by less than 0.20 mm on biting, the space can make sure that parts of the denture on the abutment teeth makes as large sinking as parts on the gingiva does.

Moreover a simple shape of the spacer is effective in making easily and with low cost the denture. As a matter of course there is no need for the spacer to make consideration on the up-side-down when using it.

(Dental magnetic attachment)

The dental magnetic attachment disclosed in the present invention is characterized by the structure of the cap.

The cap is structured by three parts, that is, the core, the sleeve, and the button. The core is placed at the designated distance of about 0.20 mm over the top of the magnetic assembly. When the biting force is loaded, the core sinks until touching to the top of the magnetic assembly. Here it is important that the designated distance is proper for sinking of the denture.

The button is put into the hollow on the top of the magnetic assembly to keep them contact at the bottom of the hollow. It supports the core over the top of the magnetic assembly. It is made of an elastic material and designed to get the proper cushion property. When biting, the pressure is concentrated on the button so that large deformation is made in the vertical direction. The button is deformed not only vertically but also horizontally according to the Poisson's ratio of the elastic material of the button by the pressure. In order to prevent the horizontal deformation from restriction of the periphery, a considerable gap between the top of the magnetic assembly and the cap is intended to remain.

On the other hand, other parts of the cap are free from the pressure, in other words, free from deformation. It assures to keep good contact with these parts and surrounding because of making no stress in the surface with them. If not so, undesirable big stress works on the interface between the cap and the magnetic assembly or the cap and the denture base. In this case, it is difficult to hold tight contact of their interface.

By the way, it is noted that there is a special case not to have the button, where too soft cushion ability is got.

The sleeve can slide along the side of the magnetic assembly on loading. But it is so tightly fit to the side that the magnetic assembly does not take off from the denture in spite of sliding. For producing good tight force, the sleeve is made of elastic material having superior elastic property. To keep the tight force over a long time, it is important that the material has a good wear resistance.

For making sure to join the cap with the magnetic assembly, it is better the the contact surface with the outer side of the magnetic assembly and the inner side of the sleeve of the cap become to be arched or tapered forward to the bottom of the magnetic assembly. If we try to remove the cap from the magnetic assembly, the arched or tapered contact surface cause strong resistance to prevent the cap from taking off.

The attachment must be held in the denture base by self curing adhesive. Tn order to prevent the cap from removing, it is desirable that a flange is built on the outer side of the sleeve of the cap going to the outer direction. The flange can make inroads into the denture base like anchor so as to offer strong retention working between the attachment and the denture base.

The cap is made of elastic material. Especially, it is preferable that the button is made of a kind of hard resin with a large elastic ratio because it shows large deformation under the given pressure. Examples of hard resin are polyvinyl acetal and silicon rubber.

It is possible that the core and the sleeve is made of non-magnetic corrosion resistant materials regardless the button is made of hard resin. Here non-magnetic corrosion resistant materials for dental use are SUS316 stainless steel, Ti alloy noble metal and so on.

One of the reason to need corrosion resistance is that if the sleeve is corroded, the corrosion of sleeve makes the sliding face more roughly and sliding on the side of the magnetic assembly becomes more resistant. The other case to show more cushion property is that the button is made of soft resin and other parts is made of hard resin.

A helper cushion can be inserted into the gap between the magnetic assembly and the cap. The effect of the helper cushion is to prevent some alien substance from entering the gap. The align substance exsiting in the gap makes damage to the cushion ability of the cap. If the helper cushion is made of foaming material such as foaming rubber and urethane foam, it shows no or little decrease of the cushion ability of the cap even if It can fill up the gap perfectly.

In the case of filling up the gap partially, the helper cushion can be made of a kind of elastic material such as silicon rubber. It is useful in weakening impact which is concentrated on the button of the cap. Other effect is to make is easy for the cap to come back to its original position by the restorative power of the material. For this restorative power, the helper cushion is applied to the type of the magnetic attachment not to have both the button of the cap and the hollow placed on the top of the amgnetic assembly.

The magnetic assembly of the present invention is characterized by the hollow on the top of it. Any structure for the magnetic assembly can be used for this invention. But in order to make a deep hollow, the magnetic assembly with a ring shaped magnet which is covered by a cap yoke preparing a projection at the center is advisable. The magnetic assembly has been described into details in Japanese Patent Application No.8-290775, i.e. Japanese Unexamined Patent Publication (KOKAI) No.10-127662. There are two reasons for the structure to offer a good cushion property. One is to make a deep hollow around the upper part of the projection of the cap yoke at the center with no effect on magnetic force. Because only a little magnetic flux flows around the upper side of the projection. A long button proportional to the depth of the hollow can be applied.

Another reason is that the ring type can make a thickness of the magnetic assembly thinner than that of the cap type without decrease of the magnetic force working between the magnetic assembly and the keeper. As the total height of the magnetic attachment including the cap and the magnetic assembly must be kept less than a critical value requested from a view point of clinical application, it is important for getting good cushion property that the button of the cap become as thick as possible but the magnetic assembly become as thin as possible. It is seen that a thick cap or button takes advantage of getting a large elastic deformation and offering good cushion.

As for magnet, it is desirable to use kinds of magnet which have high maximum energy product of more than 30 MGOe to get strong magnetic force. For example, they are Nd—Fe—B rare earth sintered magnet of more than 40 MGOe and Sm—Co rare earth sintered magnet of more than 30 MGOe. But rare earth magnet is corrosive. In order to protect it against corrosion in the oral cavity, the magnet is covered by yokes made of a soft magnetic material and sealing cases made of non magnetic material. And the boundary lines between them are welded by laser to seal up magnet. By this way, the magnet used is perfectly sealed from saliva. Here it is natural that the soft magnetic material and the non magnetic material must have good corrosion resistance because they are directly exposed in the oral cavity.

A soft magnetic stainless steel is recommended as yoke material which needs good soft magnetic property and high corrosion resistance.

As above mentioned, the present magnetic attachment consists of the magnetic assembly having the hollow on the top face and the cap which is compromised from the core, the sleeve, the flange and the button. The cushion function of the present magnetic attachment makes advantages as follows. Reducing concentration of the pressuLe on the abutment teeth, the present magnetic attachment can hold the denture on the teeth root in stability not to damage the abutment teeth. It also can solve the problem that the denture get out of place because of reducing shaking or rolling motion of the denture on biting. Moreover It can use for a long term because of not only corrosion resistant materials used but also only a little stress loaded on biting. In other words, the pressure is not so concentrated on the button to make not plastic deformation but only elastic deformation. And other parts are free from the stress.

(The method and the spacer for fixing the present magnetic attachment to the denture base)

There are two important requirements on the method and the spacer for fixing the present magnetic attachment to the denture base. One is that the sliding faces are free from a smudge of self-curing adhesive to be kept clean. Because the sleeve of the cap slides in contact with its inner face and the outer side of the magnetic attachment. Another is that the enough space is kept to make it possible to slide the front of the sleeve down. These requirements are satisfied with taking proper size in relationship with the spacer and the sleeve as follows.

First point is that the top face of the spacer is in direct contact with the front of the sleeve so as to prevent self curing adhesive from entering the boundary.

Second point is that the spacer is wider than the front of the sleeve. If not so, resin used for the denture base goes to the space made by the spacer from outer side and makes a resin overhang. This overhang obstructs the move of the front of the sleeve.

Third point is that a thickness of the spacer is equal to the sliding distance. If the thickness is less than the sliding distance, the front of the sleeve makes contact to the keeper on the root cap and is compressed to cause undesirable deformation which separates the outer side of the sleeve from the denture base made of resin.

NAME OF THE PART ACCORDING TO THE SIGN IN THE DRAWING

Figure 1:
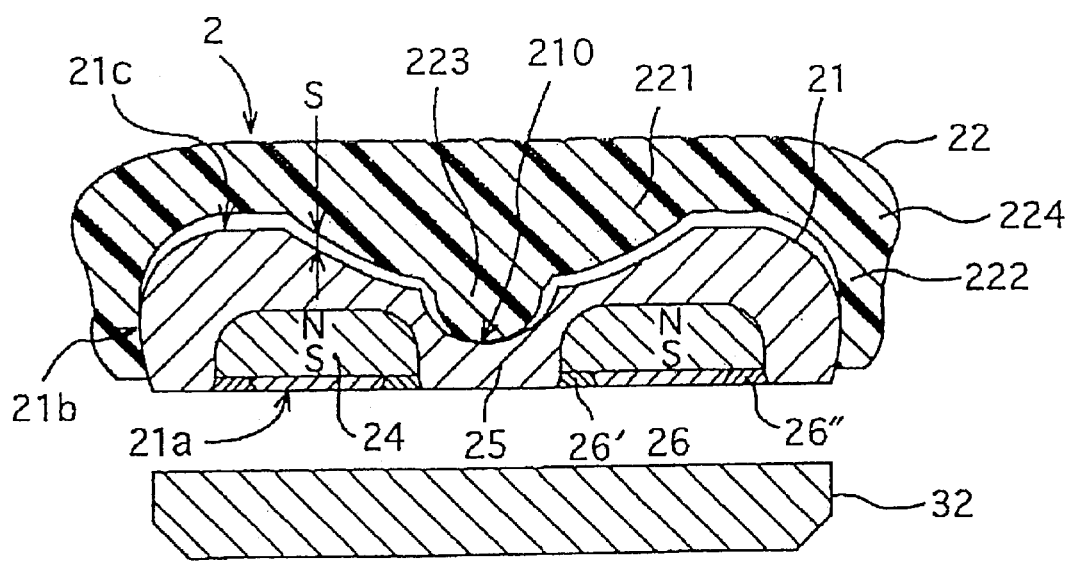
FIG. 1 is a cross section to show the construction of the first example of the magnetic attachment.

1: denture
11: artificial tooth
  12: denture base
  10: hollow of the denture base
  13: self curing adhesive
2: dental magnetic attachment
21, 21',21", 21A: magnetic assembly
  210: hollow of the magnetic assembly
  21a: contact surface
  21b: side of the magnetic assembly
  21c: top of the magnetic assembly
24: ring shaped magnet
  24': disk shaped magnet
25: cap yoke (made of the soft magnetic material)
26: ring shaped bottom yoke(made of the soft magnetic material)
26', 26", 26B: sealing ring made of the nonmagnetic material
26A: disk shaped bottom yoke(made of the soft magnetic material)
27: seat shaped magnet
  27': intermediate yoke 27": outer yoke
28: sealing case
22, 22', 22", 22A, 22B: cap
  221: core
  222: sleeve
  223: button
  224: flange
226, 226': cap cover made of hard resin
227, 227': button made of soft resin button made of soft resin
23: spacer for setting
3: root cap
31: post of the root cap,
  32, 32': keeper(made of the soft magnetic material)
  4: foam insert cushion
  4', 4": elastic insert cushion
M: magnetic flux,
  T: abutment tooth
  F: gingiva
  S: space

DESCRIPTION OF THE PREFFERED EMBODIMENTS

Nine kinds of embodiments according to the present invention is described with reference to FIG. 1 to FIG. 24.

First Embodiment
(The construction of the first example of the magnetic attachment)

Figure 4:
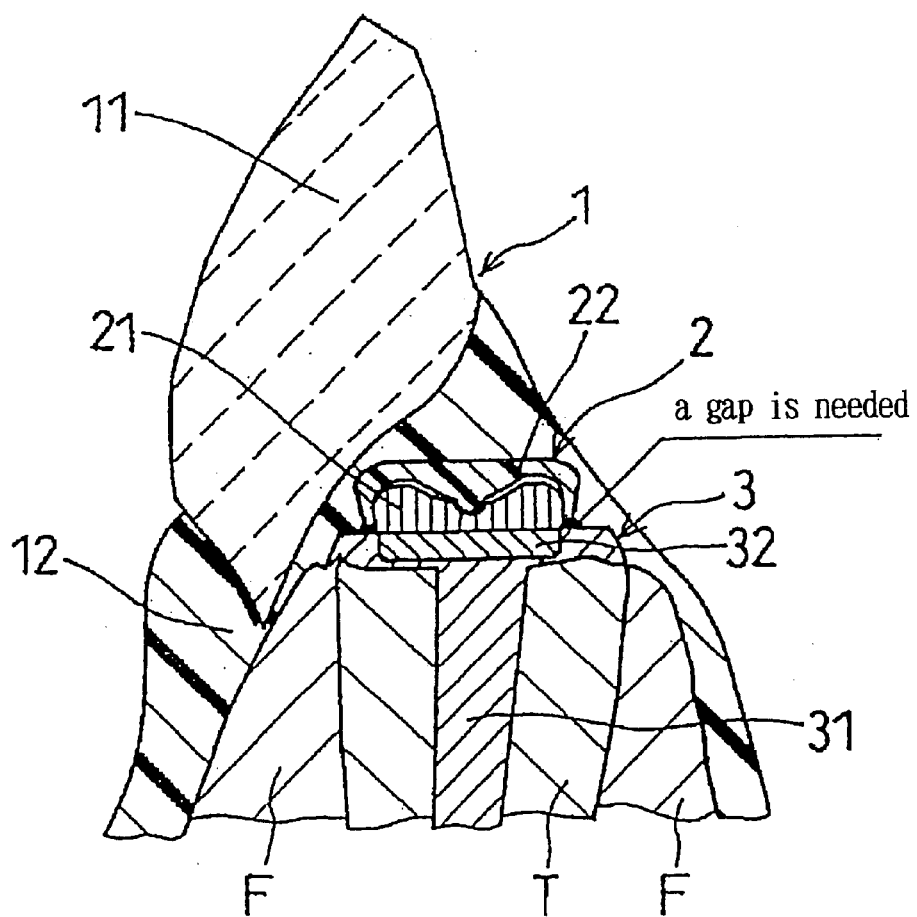
FIG. 4 is a cross section to show the relationship between the denture and the first example of the magnetic attachment.

The first example as shown in FIG. 4 is comprised with a magnetic assembly 21, a keeper 3 and a cushion cap 22. The magnetic assembly is covered by the cap 22 on the top side of it and they are unified mechanically to one. They are put into the base 12 of the denture 1. The keeper 3 is put on the teeth root T. The magnetic assembly 2 and the keeper 3 is attracted with a magnetic force.

Here the magnetic assembly 21 is compromised with a ring shaped magnet 24, a cap yoke 25 showing a complicated shape and a disk yoke 26. The magnet 24 is surrounded by the cap yoke 25 and the disk yoke 26 in the manner that a hole of the magnet 24 is filled up by the cap yoke 25. They forms a magnetic circuit to connect the magnet 24 with the keeper 32 to make a strong attractive force. Here it is important to insulate the disk yoke 26 from the cap yoke 25 magnetically. The inner sealing ring 26' and the outer sealing ring 26" are parts for magnetic insulation which prevent the disk yoke 26 from connecting magnetically with the cap yoke 25.

As seen in FIG. 4 the contact surface 21a is divided to five concentric circles of bottom faces of five parts which is a center of the cap yoke 25, a inner sealing ring 26', the disk yoke 26, a outer sealing ring 26" and the outside of the cap yoke 25 in turn from the inner side to the outer side. There is formed four contact boundaries of the center of the cap yoke 25 and the inner sealing ring 26', the inner sealing ring 26' and the disk yoke 26, the disk yoke 26 and the outer sealing ring 26", the outer sealing ring 26" and the outside of the cap yoke 25 which are welded by laser or electric beam respectively to have been in a body. The welded contact surface 21a can protect the ring shaped magnet 24 from saliva perfectly. This welded contact surface 21a also prevents the ring shaped magnet 24 from falling off from the magnetic assembly 21 when the magnetic assembly 21 is taken off the keeper 32. Because the magnet is firmly stored in the magnetic assembly 21 by means of welding.

After welding, the welded contact surface 21a is polished to a flat surface like a mirror. As a result it can attach to the keeper 32 with no gap so as to create strong attractive force between the magnetic assembly 21 and the keeper 32 placed on the root cap 3. By the strong force, the denture 1 can be held stably on the abutment teeth in the oral cavity The most advantage for the above mentioned magnetic assembly 21 is that it can furnish a deep hollow 210 on the top of the cap yoke 25 without the decrease of the magnetic attractive force because only a little magnetic flux flow around the center part of the top of the magnetic assembly 21c in this magnetic circuit using the ring shaped magnet 24.

The cap 22 is made of a hard resin in a body which consists of a core 221 and a sleeve 222 as two region. The core 221 is placed at the designated distance, for example about 0.20 mm, over the top of the magnetic assembly 21. When the biting force is loaded, the core is dislocated until touching to the top of the magnetic assembly 21c. The sleeve 222 formed around the core is tightly fit to the side of the magnetic assembly 21b in the condition that it can slide but does not take off.

The present magnetic attachment is an assembly with the cap 22 and the magnetic assembly 21. For assembling, the cap 22 is placed on the top of the magnetic assembly setting a button 223 into the hollow 210, and then is pressed under a given pressure to become one. The side of the magnetic assembly is shaped round. The middle part of the side has a maximum diameter and the upper part of side is tapered to become smaller in diameter going near the top. When pressed, the magnetic assembly 21 can be inserted easily into the cap 22. This round shaped side is favorable for inserting the magnetic assembly into the cap 22 under the given pressure, so that it is furnished in every examples.

It is noted that the given pressure for inserting is set much larger than the magnetic attractive force working between the magnetic assembly and the keeper 32. Therefore when the magnetic assembly is taken apart from the keeper 32 by the same force to the magnetic attractive force, the magnetic assembly is not taken off from the cap 22.

A preferable structure of the present magnetic attachment is composed of the magnetic assembly has a hollow on the center of the top surface. On the other hand the cap 22 has a button 223 on the inner surface of the core 221 which is inserted in contact with the bottom of the hollow. On non-loading, there remains a proper gap S between the top of the magnetic assembly 21a and the core 221. The button 223 is attached to the top of the magnetic assembly 21c in the condition that they are contact only at the center point of the bottom of the hollow 210 together and there are some space around the button 223, that is, between the button 223 and the hollow 210 except the center point. This space is enough large to allow the button 223 to deform in the horizontal direction when the button 223 is compressed by the pressure in biting. On the other hand the cap 22 is not deformed in the horizontal direction. Because it is nearly free from the pressure. Most of the pressure is concentrated on the button 223.

When the biting force is loaded, the sleeve 222 slides along the side of the magnetic assembly 21b and the core 221 approaches to the top of the magnetic assembly 21c through the space(S). But the space(S) is designed to be not less than the maximum distance for sinking of the denture, so the core 221 can go down at most until touching to the top of the magnetic assembly. In this manner, the cap 22 which is made of hard resin is free from the pressure so that it is not deformed in the horizontal direction as well as in the vertical direction.

Figure 2:
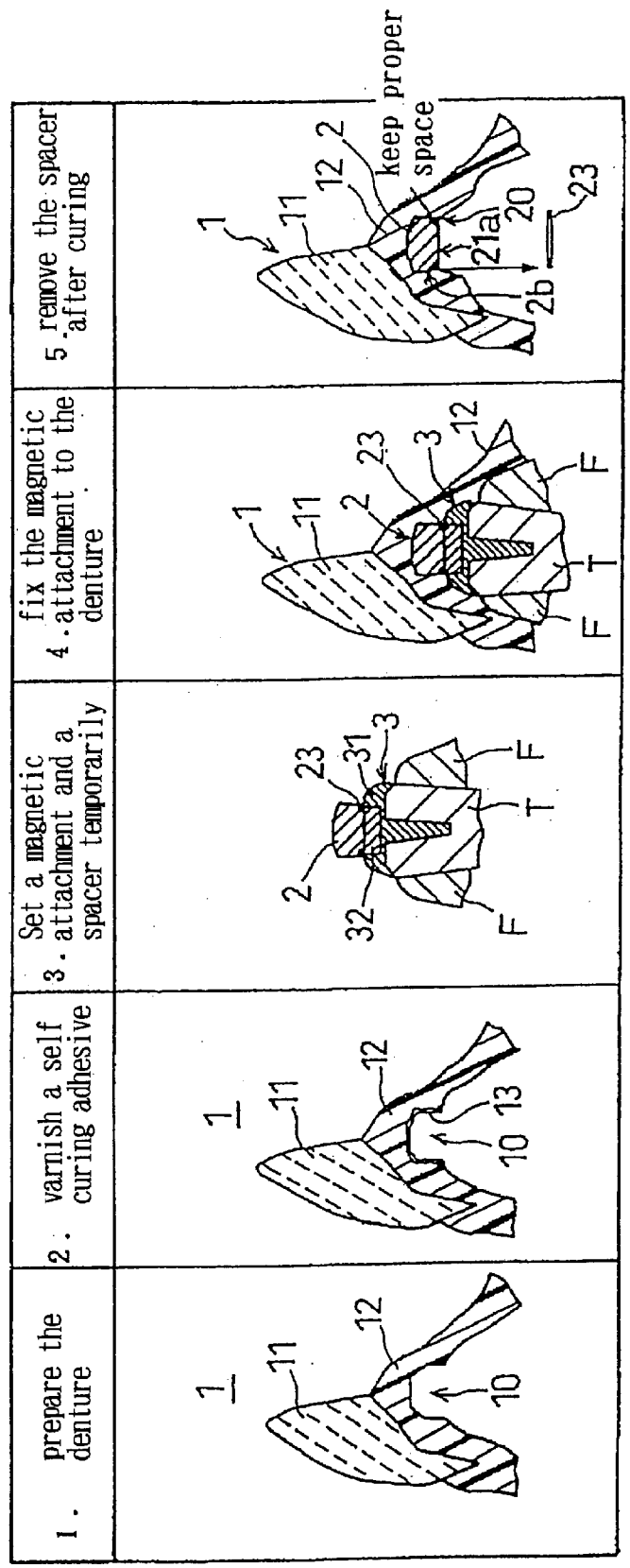
FIG. 2 is an illustration for explaining the procedure in the fixing method to fix the first example of the magnetic attachment.

It means that the cap 22 can be kept good contact with a hollow10 of the denture base 12 by self curing resin as shown in FIG. 2, because no stress occurs on the interface with them.

A flange 224 is built on the outer side of the sleeve 222 going to the outer direction. It can make inroads into the denture base 12 like anchor so that the attachment 2 is held firmly in the denture base 12. Even if separation is made partially on the interface with them, the anchor effect prevents the attachment 2 from taking off the denture base 12.

Figure 5:
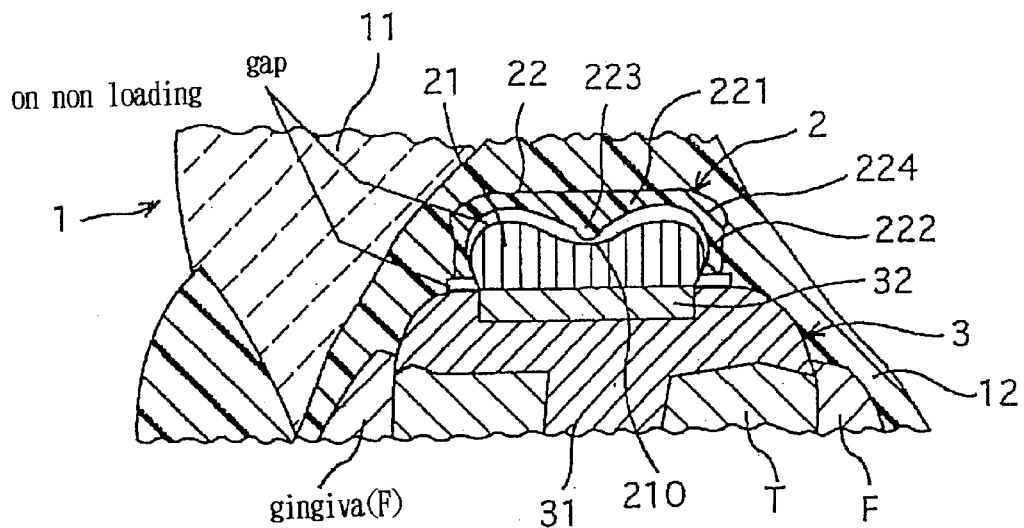
FIG. 5 is a cross section to show the location of the first example of the magnetic attachment on non loading.
Figure 6:
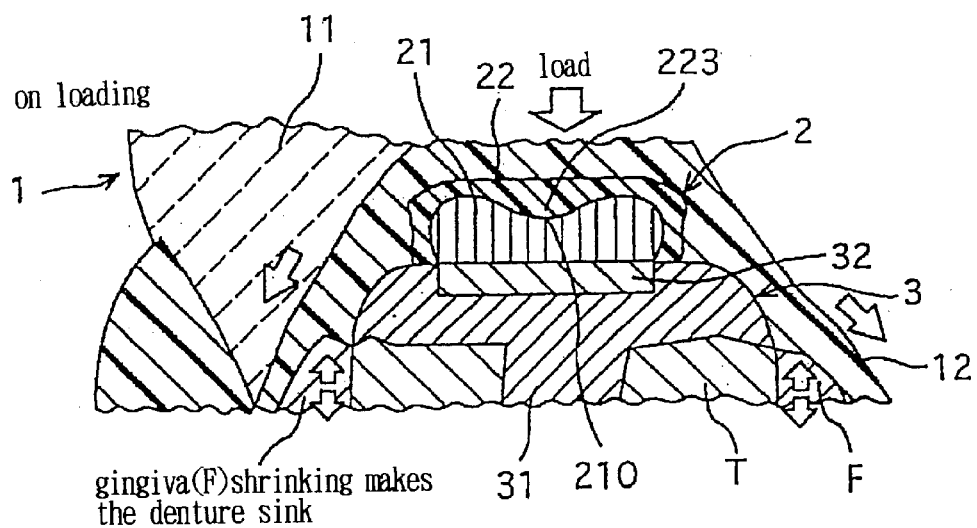
FIG. 6 is a cross section to show the location of the first example of the magnetic attachment on biting.

It is seen in FIG. 5 and 6 that on biting, the biting pressure makes the cap 22 of the magnetic attachment 2 slide and approach to the magnetic assembly 21. So that the denture base 12 sinks into the gingiva(F). On the contrary, when the biting force is released, the elasticity of the gingiva(F) makes the righting moment for lifting up the denture 12. The moment makes the cap 22 to slide reversely along the magnetic assembly 21 and to return back to the beginning position.

As shown in FIG. 1, the side 21b of the magnetic assembly 21 is arched or tapered forward to the contact surface 21a. It is pressed against the inner side of the sleeve 222. Removing the cap 22 from the magnetic assembly 21, the arched or tapered contact surface causes a strong resistance to prevent the cap 22 from taking off.

Here the magnetic assembly 21 is compromised with the ring shaped magnet 24, the cap yoke 25, the disk yoke 26 and two sealing ring 26' 26". They forms a magnetic circuit to connect the magnet 24 with the keeper 32 in which two sealing ring insulate the disk yoke 26 from the cap yoke 25 magnetically. The ring shaped magnet 24 is made of Nd—Fe—B rare earth sintered magnet of more than 40 MGOe. Both the cap yoke 25 and the disk yoke 26 are made of a soft magnetic stainless steel. Both the sealing rings 26',26" are made of a non magnetic stainless steel.

The cap 22 is made of polyvinyl acetal resin or hard polyoxymethylene resin.

Hereafter the effect of the first example is described. FIG. 4 shows a cross section of the denturel with the present magnetic attachment 2 placed on an abutment tooth in a oral cavity. The denture 1 consists of plural artificial teeth 11, a denture base 12 and the present magnetic attachment 2 which is put in a hollow 10 of the denture base 12 and is cemented by a self curing resin. A flange 224 which is built on the outer side of the sleeve 224 going to the outer direction can prevents the attachment 2 from taking off the denture base 12. Because it makes inroads into the denture base like anchor. The cap 22 is assemblyd firmly with the magnetic attachment 21.

The magnetic attachment 2 is attached to the keeper 32 bedded into the root cap 3 in the abutment toothT by the magnetic attractive force, so that the denture base 12 is kept in the oral cavity.

On biting, the present magnetic attachment 2 shows a large shrinking due to the elastic deformation of the button 223 on which the biting force makes a concentration. In other words, the present magnetic attachment 2 put in the denture 1 has a superior cushion property.

At this time, the cap 22 except the button 223 is hardly deformed, so as to give no cyclic mechanical stress to the contact surface with the cap 22 and the magnetic assembly 21 as well as the cap 22 and the denture base 12. As a result, these contacts shows good endurance. There is no trouble to take the magnetic assembly 21 off from the denture base 12 and to remove the cap 22 from the magnetic assembly 21.

This cushion property of the present magnetic attachment 2 can absorb the cyclic pressure so as to prevent the denturel from shaking. Speaking in details, the shaking motion occurs by large difference of the displacement between the part on the abutment teeth and the part on the gingiva. This cushion property makes to sink the part on the abutment toothT by same degrees to the part on the gingiva so that a little difference of the displacement is made to prevent the denturel from shaking.

The cap 22 can make seesaw motion or lean on the magnetic assembly 21 within the limit of elastic deformation of the sleeve against the side 21b of the magnetic assembly 21. If it has a round shape, the angle of the lean or seesaw motion may become to be large. This property of the cap 22 makes it possible to lean the denture base 12 to a given degree, with keeping the magnetic assembly contact on the keeper 32. Even if the denture lean under normal conditions there is no trouble that the denture 1 remove from oral cavity.

Summing up the above effect of the present magnetic attachment 2 is as follows. On biting, the denture 1 having the present magnetic attachment 2 tends to sink uniformly on the abutment teeth(T) for the cushion property. Uniformly sinking makes no concentration of the pressure on the abutment teeth(T). It means that the abutment teeth(T)is kept to be in a good condition. This cushion property also restrains shaking of the denture 1 on the abutment teeth(T). And it also can lean the denture 1 on the abutment teeth(T) keeping contact with the magnetic asembly 21 and the keeper 32. That is, it offers a merit to hold the denture 1 firmly in oral cavity due to the cushion property as well as the strong magnetic attractive force. Moreover, It is important that the magnetic attachment 2 is made of corrosion resistant materials to get a long life in use (The method for fixing to the denture)

The method for fixing the present magnetic attachment 2 to the denture 1 consists of three steps named as setting step, fixing step and removing step in turn. The first setting step is for setting the present magnetic attachment 2 into the hollow 10 of the denture 1 shown in FIG. 2. The second fixing step is for fixing them by self curing adhesive and the third removing step is for removing a spacer 23.

A spacer 23 for fixing the denture 1 which is a ring in shape is used temporally to keep the space under the sleeve around the magnetic assembly. It is assemblyd with the magnetic assembly 21 to be set under the sleeve 222 in FIG. 3. The magnetic attachment 2 together with the spacer 23 is inserted into the hollow 10 of the denturel, then fixed by self curing adhesive. At this time the spacer 23 prevent the self curing adhesive from entering the space.

Briefly speaking, this method to fix the magnetic attachment 2 to the denture base 12 is characterized by using the spacer 23.

The first step for setting the present magnetic attachment 2 into the hollow 10 of the denture 1 with self during adhesive is shown in FIG. 2.

In FIG. 2 is shown the denture 1 which is comprised with the denture base 12 made of resin (polymethylene methacrylate) and artificial teethll made of resin (polymethylene methacrylate). FIG. 2-1 shows the hollow 10 of the denture base 12. FIG. 2—2 shows that self curing adhesive 13 (acrylic resin)is varnished on an inner side of the hollow 10.

Figure 3:
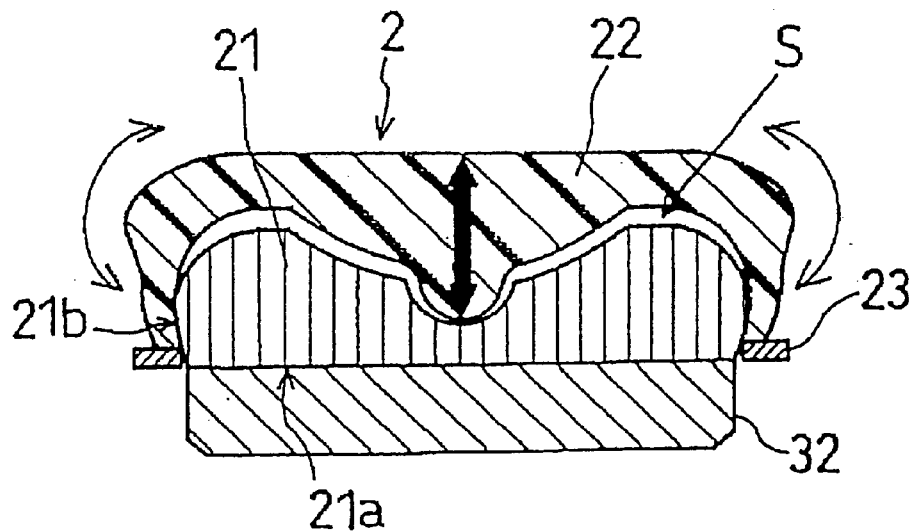
FIG. 3 is a cross section to show the function of the spacer for setting the first example.

FIG. 2–3 shows that the magnetic attachment 2 which is assemblyd with the spacer 23 is placed on the keeper 32 to be strongly attached together by the magnetic attractive force.

Next is about the second step for fixing them by self curing adhesive. FIG. 2–4 shows the magnetic attachment 2 fixed with the denture 1 by self curing resin. As soon as self curing resin is varnished, a dentist must insert the magnetic attachment 2 into the hollow 10 of the denture 1 in oral cavity. For a while the magnetic attachment 2 with the spacer 23 is fixed there by self curing adhesive. The spacer 23 is put at the position under the sleeve 222 around the magnetic assembly 21. After it is removed, the place becomes the space which makes it possible to slide the cap 22 along the side 21b of the magnetic assembly. The spacer 23 fills up the space, so that it is effective for preventing the self curing adhesive from entering into the space. In other words, first a dentist continues to press the denture 1 in several minute in oral cavity of a patient. For a wile the self curing resin on the whole surface of the cap 22 become soldering or curing by itself. At last the magnetic attachment 2 is firmly fixed in the hollow 10 of the denture base 12.

When there is the excess of the self curing adhesive, it is going out from the space with the cap and the hollow of the denture base. The spacer 23 prevent the excess of the self curing adhesive from entering the space at the front of the sleeve. Even if there is too much excess of the adhesive, there remains the space to make it possible to slide the cap along the side of the magnetic assembly.

Last, the third step for removing a spacer 23 is shown using FIG. 2–5. After the second step, the denturel is taken off from the oral cavity of the patient and then the spacer 23 is removed from the denture base 12 with a pair of tweezers. After the sapcer 23 is removed, the space is made at the former position of the spacer 23. And an enough space for the sliding of the sleeve 222 is kept.

Therefore the cap 22 can slide down along the side 21b of the magnetic assembly 21 by a distance equal to the thickness of the space and give a good cushion property to the denture having the present magnetic attachment 2. This cushion property offer advantages to protect the abutment teeth(T) from the harmful pressure and hold the denture 1 stable in oral cavity.

(Effects of the fixing method of the First Embodiment)

The above mentioned method is useful for making sure to fix the magnetic attachment 2 in the denture base 12 by enough volume of self curing adhesive. Moreover the method offers other advantages to keep the space needed for the chusion property on biting without a considerable training and a troublesome adjustment to remove excess of the adhesive.

(Dimensions and materials of the spacer of the First Embodiment)

The spacer has a inner diameter of 0.2 mm plus the outer diameter of the and a thickness nearly equal to the maximum stroke of sinking. That is, the denturel cannot sink more than the thickness of the spacer 23. The spacer is made of any material but a harmful one against a human body, and it is better that the material can take off easily from the self curing adhesive and it has a moderate hardness.

The ring shaped spacer of an example, in a case of 3.9 mm in a outer diameter of the magnetic assembly 21 and 0.2 mm in the maximum depth of sinking, has a inner diameter of 4.1 mm, a outer diameter of 5.0 mm and a thickness of 0.2 mm, and it is made of aluminum.

The ring shaped spacer of the second example, in a case of 3.4 mm in a outer diameter of the magnetic assembly 21 and 0.1 mm in the maximum depth of sinking, has a inner diameter of 3.6 mm, a outer diameter of 4.6 mm and a thickness of 0.1 mm, and it is made of SUS304 stainless steel.

The ring shaped spacer of the third example, in a case of 4.4 mm in a outer diameter of the magnetic assembly 21 and 0.4 mm in the maximum depth of sinking, has a inner diameter of 4.6 mm, a outer diameter of 6.0 mm and a thickness of 0.4 mm, and it is made of hard rubber.

(The first modified fixing method)

There are some modified spacer to make it possible to disappear the spacer.

If a proper material of the spacer 23 is used, it is possible to skip the third step for removing the spacer 23. Supposing the material is readily soluble or is sublimated in oral cavity without ill effects against a human body, the sacer 23 disappears by itself.

(The second modified fixing method)

If necessary, we can operate the fixing procedure outside oral cavity in stead of operating in oral cavity. The method is done with a procedure as follows.

First, the model for the maxilla is maae through molding in the oral cavity of a patient. Next, the magnetic attachments are put on certain places of the model. Then, hollows 10 of the denture base12 are made opposite to the places for setting the magnetic attachments. After that, the adhesive 13 is varnished on the inner side of the hollow 10. As soon as possible, the denturel is placed on the model for the magnetic attachment 2 is fixed to the hollow of the denture. After curing, the denture takes off from the model. last, the spacer 23 is removed to make the space for the denturel to sink.

The merits operating in the outside are that both dentists and technicians can operate it very easily, and a physical or mental pain of a patient decreases considerably. Of course, there is a demerit that molding procedure needs some time. In addition, the outside operating method is applied with a self curing adhesive 13 having a high curing temperature.

(The third modified fixing method)

There are some modified method that the self curing adhesive does not varnish on the hollows.

For example, it is possible that the self curing adhesive 13 will be put on the top of the magnetic attachment which is set on the keeper 32. In this case, covering with the denture makes the adhesive 13 spread into the hollow 10 all over.

For other example, the top of the cap 22 in the magnetic attachment is coated with the self curing adhesive 13, cooled in the refrigerator and so on. After it is inserted into the hollow 10 of the denture base 12, the self curing adhesive 13 is warmed to go into a liquid state. Then, the adhesive 13 which is a kind of therm setting resin, is cured to fix the magnetic attachment 2 to the denture 1.

For special example, a mother resin is varnished either on the top of the cap 22 of the magnetic attachment 2 or on the inner surface of the hollow 10 of the denture base 12. On the other surface, a cure accelerator is varnished. When the denture base 12 is placed on the magnetic attachment 2 with the spacer 23, both resins are mixed to start curing.

Three above modified method can offer same merits as the fixing method for the first example.

(Other modified fixing method)

This case is related to materials used.

The artificial teethll can be made of resin and ceramics besides several kinds of resin. The denture base 12 can be made of metals such as titanium, which is not harmful against a human body except resin. For the self curing adhesive, self curing resin 13 except acryloyl and many kinds of thermal setting resin are useful.

These materials can offer same merits as the fixing method for the first example.

(Dimensions of the first example)

Figure 7:
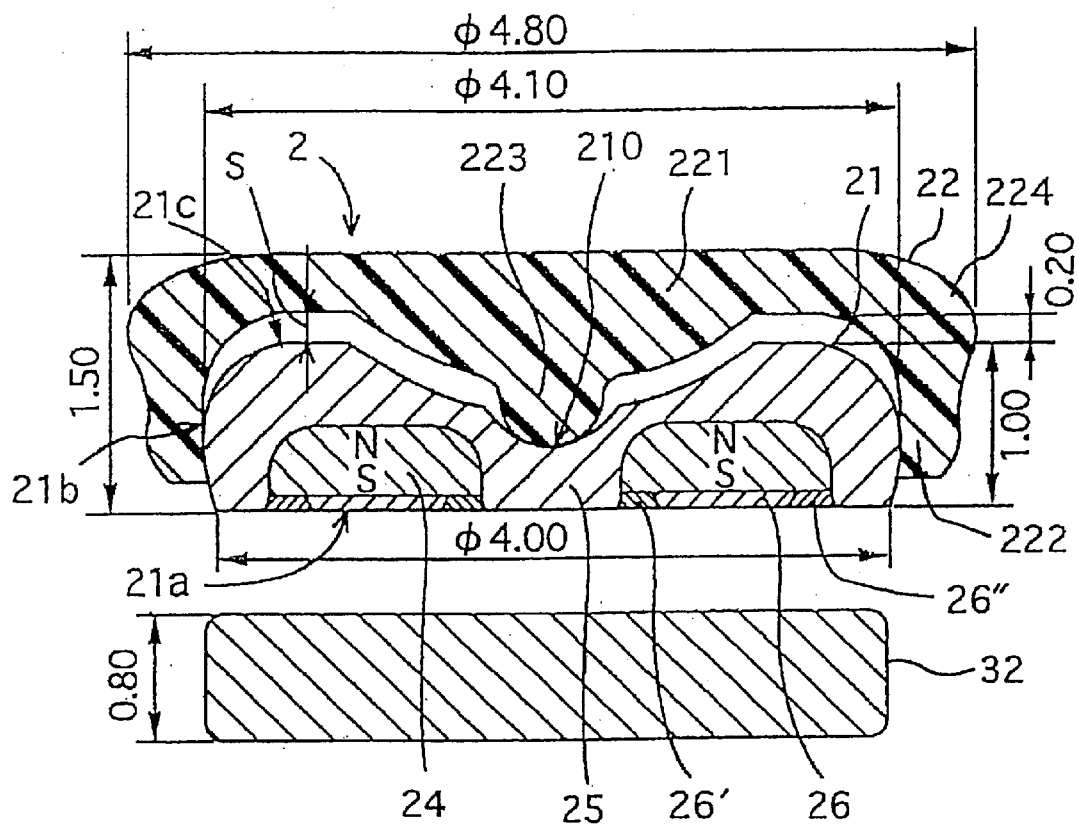
FIG. 7 is a cross section to show dimensions of the first example of the magnetic attachment.

For reference, FIG. 7 shows the detail dimensions of the first example. Almost dimensions of the parts can be picked up from this figure, since the present magnetic attachment is symmetrical with respect to the center axis.

Second Embodiment

Figure 8:
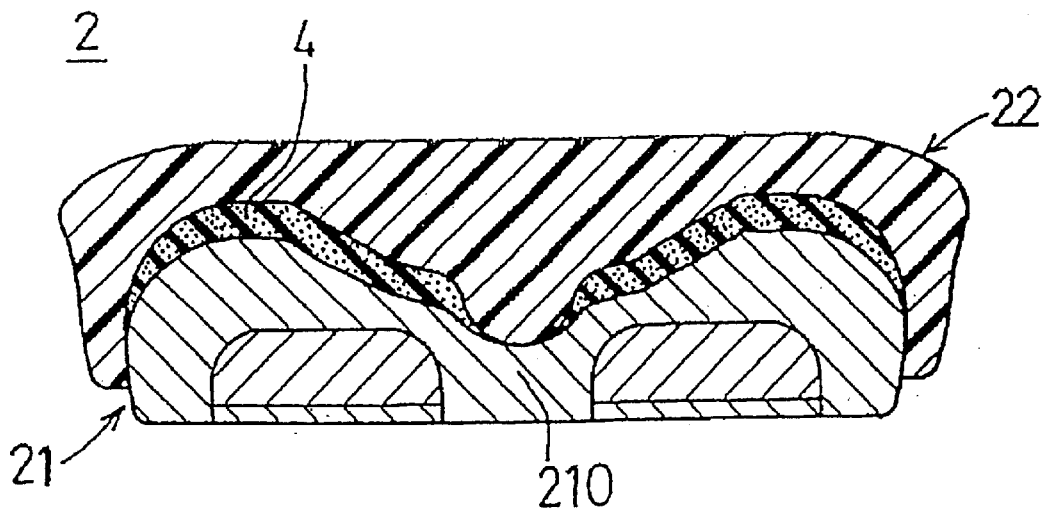
FIG. 8 is a cross section to show the construction of the second example of the magnetic attachment.

FIG. 8 shows a cross section of the second example of the magnetic attachment in which a helper cushion 4 made of foaming material such as foaming rubber and urethane foam is inserted into the gap between the magnetic assembly 21 and the cap 22.

The helper cushion makes the effect to prevent some alien substance from entering the gap without reducing the cushion property.

Third Embodiment

Figure 9:
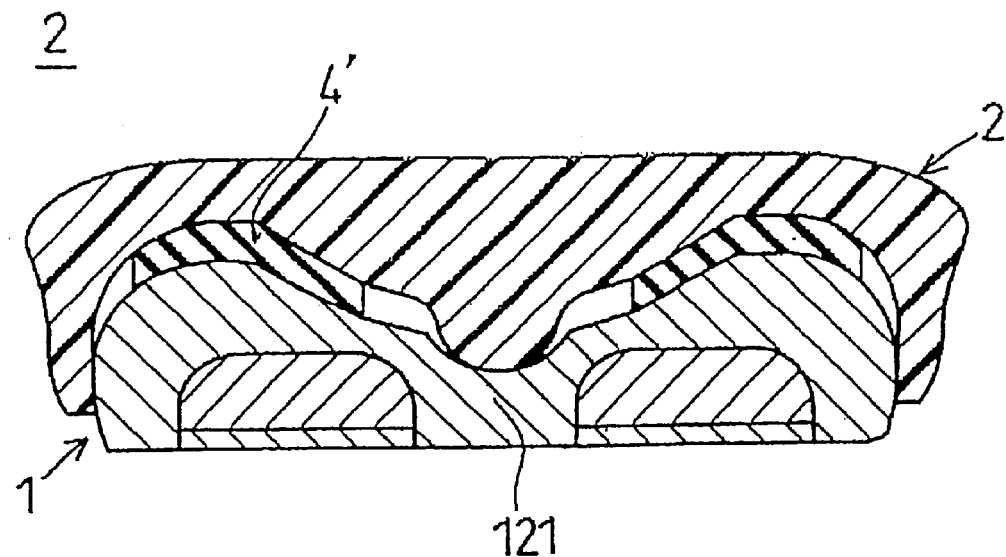
FIG. 9 is a cross section to show the construction of the third example of the magnetic attachment.

FIG. 9 shows a cross section of the third example same to the second example except the following points. One is that the helper cushion 4' is made of elastic rubber such as silicon rubber. The second point is that the gap between the magnetic assembly 21 and the cap 22 is filled up partially by the helper cushion 4'.

The helper cushion makes the same effect to the second example and in addition, to reduce the impact by elastic compression when the cap 22 collides against the top of the magnetic assembly 21.

Fourth Embodiment

Figure 10:
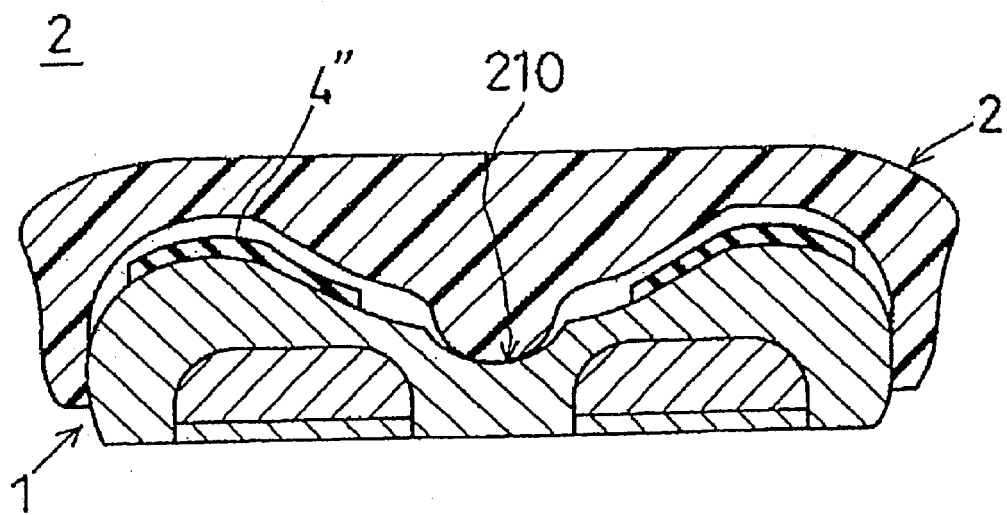
FIG. 10 is a cross section to show the construction of the fourth example of the magnetic attachment.

FIG. 10 shows a cross section of the fourth example nearly equal to the third example except a thickness of the helper cushion 4". The helper cushion 4' is not directly contact to the cap 22 because of a smaller thickness than a height of the gap between the magnetic assembly 21 and the cap 22.

The helper cushion 4" makes not only the effect same to the third example, but also an improved cushion property. That is, when this magnetic attachment 2 is deformed, the first stage of deformation goes smoothly through elastic deformation of the button 223 and at the last stage when the cap collides against the top of the magnetic assembly, the impact is reduced by an elastic compression of the helper cushion 4".

Fifth Embodiment

Figure 11:
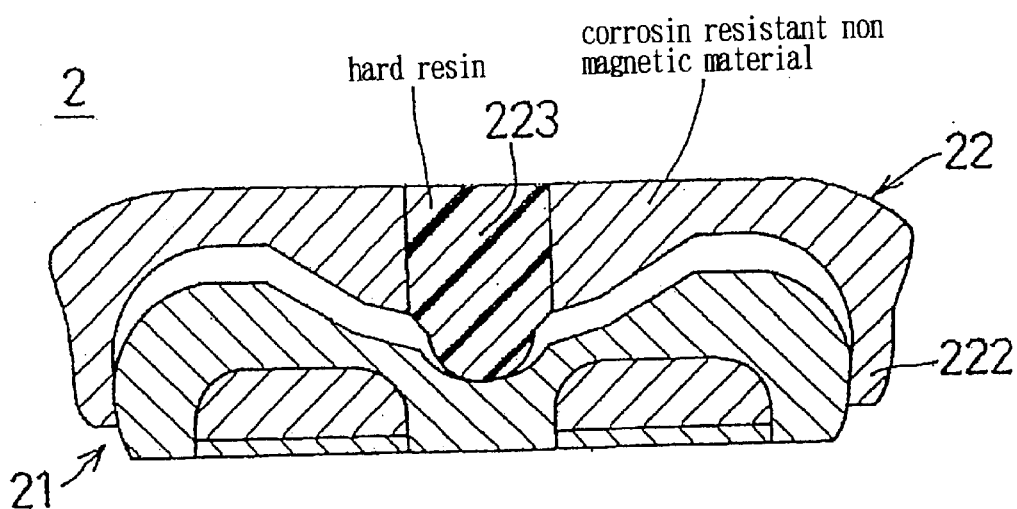
FIG. 11 is a cross section to show the construction of the fifth example of the magnetic attachment.

FIG. 11 shows a cross section of the fifth example of the magnetic attachment 2 in which a button 223 is made of a hard resin and other parts of the cap 22 including the sleeve 222 is made of a corrosion resistant non-magnetic material. Here the hard resin used is polyvynyl acetal, and the corrosion resistant non-magnetic material used is SUS316 stainless steel.

The fifth example has the good property same to the first example and in addition, it has an improved cushion property through an improved elastic button 223.

Sixth Embodiment

Figure 12:
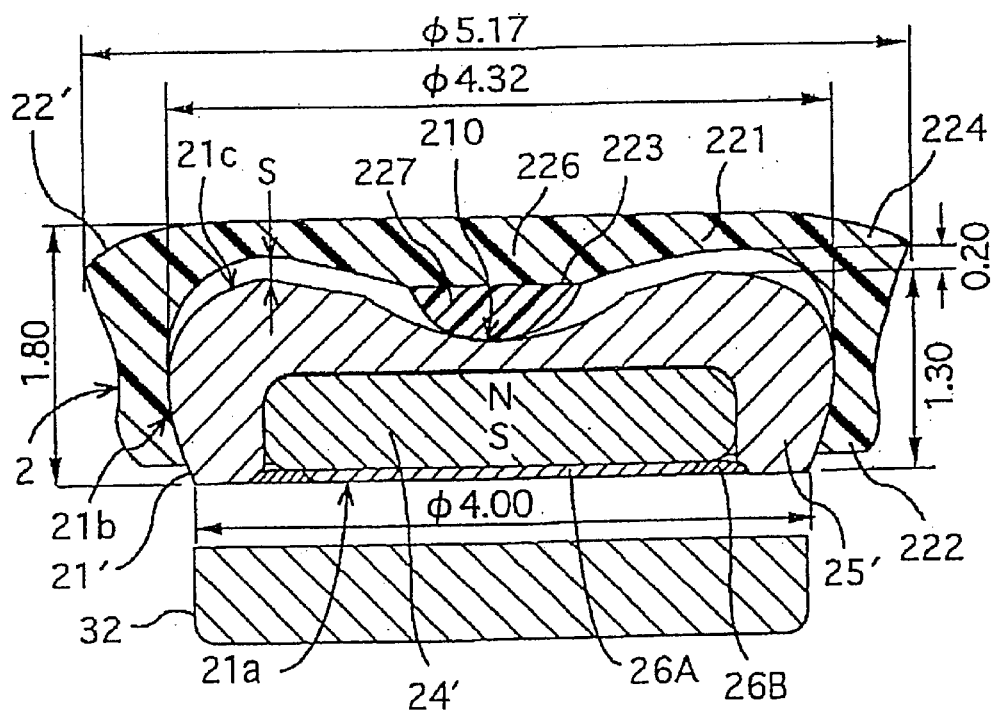
FIG. 12 is a cross section to show the construction of the sixth example of the magnetic attachment.

As shown in FIG. 12, the sixth example of the magnetic attachment 2 consists of a cap 22' covered the magnetic assembly 21' and a magnetic assembly 21' attached to a keeper 32 with an attractive magnetic force.

The magnetic assembly 21' is compromised with a ring shaped magnet 24', a cap yoke 25' showing a symmetrical shape with respect to the center axis, a disk yoke 26A and a sealing ring 26B. The magnet 24 is surrounded by the cap yoke 25' and the disk yoke 26A. They forms a magnetic circuit to connect the magnet 24' with the keeper 32 to make a strong attractive force.

Here it is important to insulate the disk yoke 26A from the cap yoke 25' magnetically. The sealing ring 26B is a part for magnetic insulation which prevent the disk yoke 26 from connecting magnetically with the cap yoke 25. As seen in FIG. 12 the contact surface 21a is divided to three concentric circles of bottom faces of three parts which is the disk yoke 26A, the sealing ring 26B and the cap yoke 25' in turn from the inner side to the outer side.

There are both contact boundaries the sealing ring 26' with the cap yoke 25' and the disk yoke 26A respectively which are welded by laser or electric beam to have been in a body. The welded contact surface 21a can perfectly protect the disk shaped magnet 24' which is corrosive from saliva.

After welding, the welded contact surface 21a is polished to a flat surface like a mirror. As a result it can attach to the keeper 32 with no gap so as to create strong attractive force between the magnetic assembly 21' and the keeper 32 placed on the root cap 3. By the strong force, the denturel can be held stably on the abutment teeth(T) in the oral cavity as shown in FIG. 4.

The cap 22 consists of a cap-cover 226 and a soft resin button 227. The cap-cover 226 is divided into a core 221 and a cap slleve 222. The soft resin button 227 is made of a soft POM(polyoxymethylene resin) which offers a good cushion property. On the contrary, the cap-cover 226 is made of a hard POM(polyoxymethylene resin).

The soft resin button 227 is contact to both the cap-cover and the top of magnetic assembly. And it lifts up the cap-cover 226 at the designated distance (S) over the top 21C of the magnetic assembly 21'. The cap-cover 226 is formed with a hard resin as a body wihch is comprised of the core 221 and the cap-slleve 222. The sleeve 222 is tightly fit to the side 21b of the magnetic assembly 21' in the condition that it can slide but does not take off.

The side 21b of the magnetic assembly 21 which is contact to the sleeve 222 is arched or tapered forward to the contact surface 21a. The inner side of the sleeve 222 tighten the magnetic assembly 21' strongly. So removing the cap 22' from the magnetic assembly 21', the arched or tapered contact surface causes a strong resistance so as to prevent the cap 22 from taking off.

The magnetic assembly 21' has a hollow 210 on the center of the top surface. On the other hand the cap 22 has the soft resin button 227 which is attached to the inner surface of the core 221 and at the same time in contact with the bottom of the hollow. On non-loading, there remains a proper gap(S) between the top of the magnetic assembly 21c and the core 221.

The soft resin button 227 is attached to the top of the magnetic assembly 21c in the condition that they are contact only at the center point of the bottom of the hollow 210 together and there are some space around the button 223, that is, between the button 223 and the hollow 210 except the center point. This space is enough large to allow the soft resin button 227 to deform in the horizontal direction when the soft resin button 227 is compressed by the pressure in biting. On the other hand the cap 22 is not deformed in the horizontal direction. Because it is nearly free from the pressure. Most of the pressure is concentrated on the button 223.

When the biting force is loaded, the sleeve 222 slides along the side of the magnetic assembly 21b and the core 221 approaches to the top of the magnetic assembly 21c through the space(S). But the space(S) is designed to be not less than the maximum distance for sinking of the denture, so the core 221 can go down at most until touching to the top of the magnetic assembly. In this manner, the cap 22' which is made of hard resin is free from the pressure so that it is not deformed in the horizontal direction as well as in the vertical direction. It means that the cap 22' can be kept good contact with a hollow 10 of the denture base 12 by self curing resin as shown in FIG. 2, because no stress occurs on the interface with them.

A flange 224 is built on the outer side of the sleeve 222 of the cap 22' going to the outer direction. It can make inroads into the denture base 12 like anchor so that the attachment 2 is held firmly in the denture base 12. Even if separation is made partially on the interface with them, the anchor effect prevents the attachment 2 from taking off the denture base 12.

Summing up effects of the sixth example is as follows. The sixth example has not only the effect same to the first example but also an improved cushion property to deform softly against the pressure because the soft resin button 227 is made of a soft resin instead of a hard resin. In addition, the sixth example offers an possibility to be made more cheap than the first example because of the simple structure of the magnetic assembly 21'.

Seventh Embodiment

Figure 13:
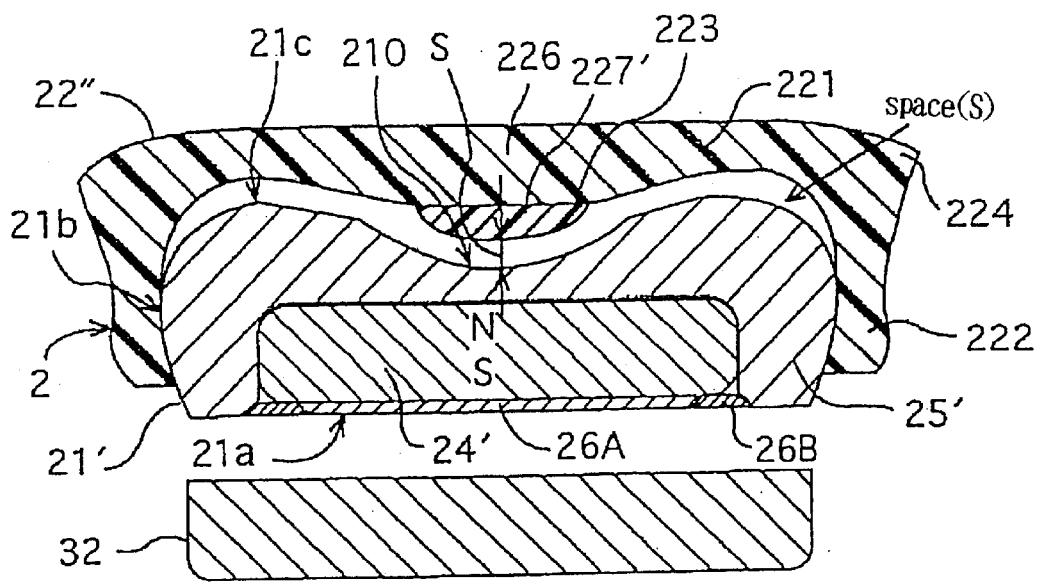
FIG. 13 is a cross section to show the construction of the seventh example of the magnetic attachment.

FIG. 13 shows a cross section of the seventh example same to the sixth example except that a length of the soft resin button 227 of the cap 22" is smaller than that of the sixth example. There is a small gap(S) between the hollow 210 of the magnetic assembly 21' and this half size one of the soft resin button 227 on non-loading.

Figure 14:
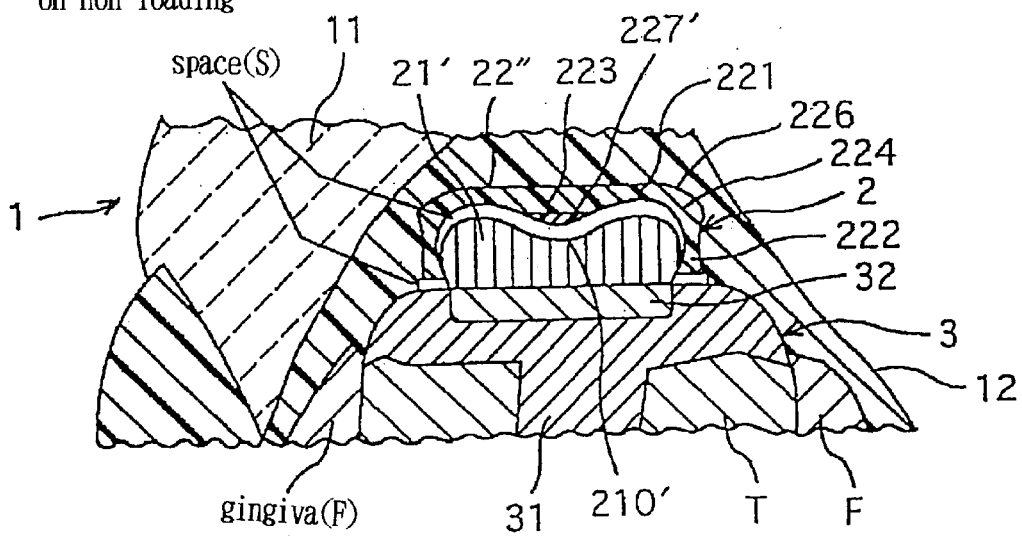
FIG. 14 is a cross section to show the location of the seventh example of the magnetic attachment on non loading.
Figure 15:
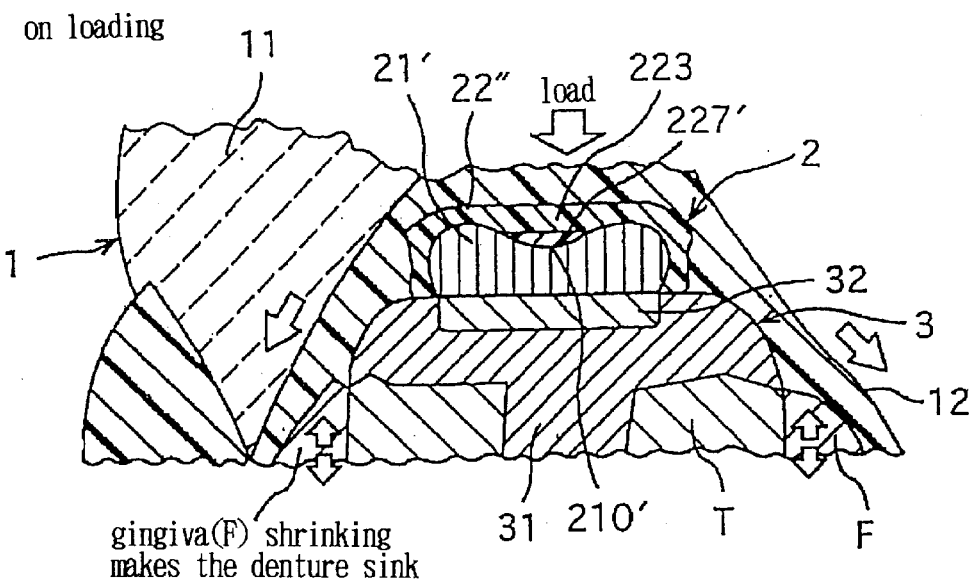
FIG. 15 is a cross section to show the location of the seventh example of the magnetic attachment on biting.

Therefore at just moment on loading as shown in FIG. 14, no repulsion force due to compression of the soft resin button 227 occurs. It means that the denturel is supported only by gingiva(T) even if the part is on the abutment teeth. In a very small while, the tip of the soft resin button 227 is reached to the hollow 210 and after that, repulsion forces according to degrees of compression of the soft resin button 227 occur. When the maximum of the biting force is loaded, the cap can sink until the core 221 will reach to the top surface 21c of the magnetic assembly and both surfaces are fully contact as shown in FIG. 15.

This half size one of the soft resin button 227 makes merits that if a biting force is more than a repulsion force of the gingiva, the magnetic attachments on the abutment teeth makes some repulsion force to protect the gingiva. If a biting force is less than a repulsion force of the gingiva, the denture sink uniformly to give a patient a good and soft feeling.

Eighth Embodiment

Figure 16:
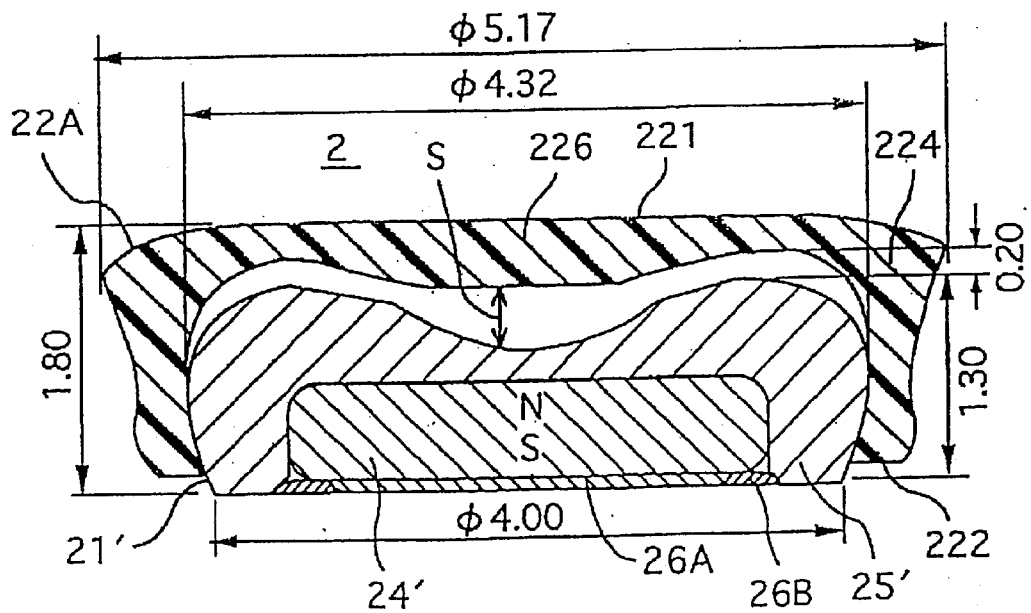
FIG. 16 is a cross section to show the construction of the eighth example of the magnetic attachment.

FIG. 16 shows a cross section of the eighth example same to the sixth example or the seventh example except that it has no soft resin button 227 of the cap 22A. The cap 22A of the eighth example is comprised only of the cap-cover 226 made of a hard POM resin without the button 223.

Figure 17:
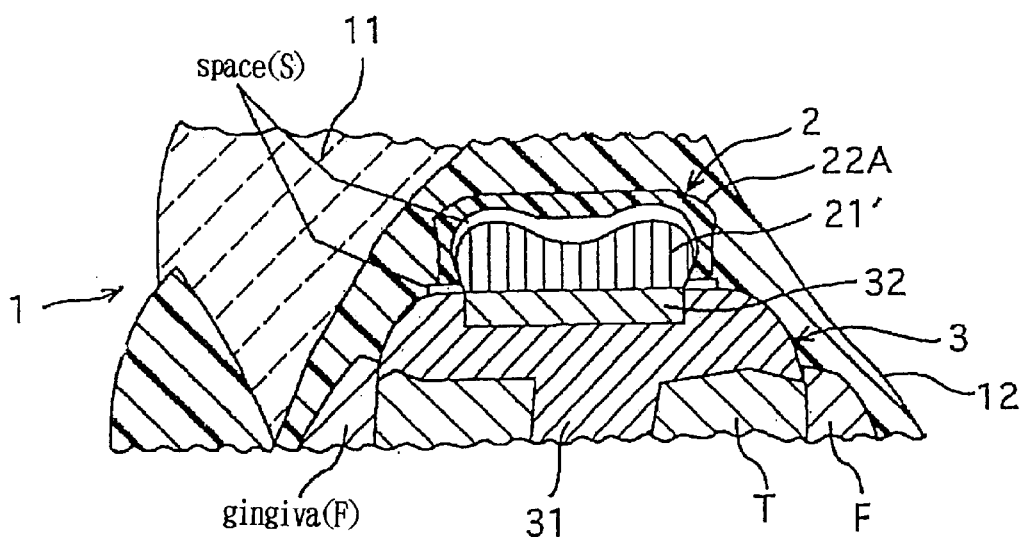
FIG. 17 is a cross section to show the location of the eighth example of the magnetic attachment on non loading.
Figure 18:
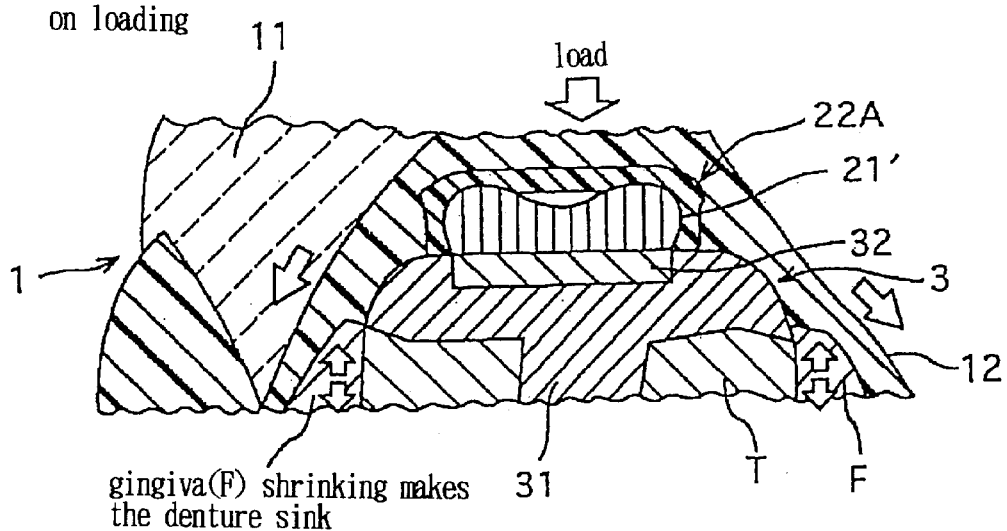
FIG. 18 is a cross section to show the location of the eighth example of the magnetic attachment on non loading.

The eighth example has not only the effect same to the seventh example as shown in FIG. 17 and FIG. 18, but also offers an possibility to be made more cheap because the cap 22A is molded at one shot of a hard resin.

Ninth Embodiment

Figure 19:
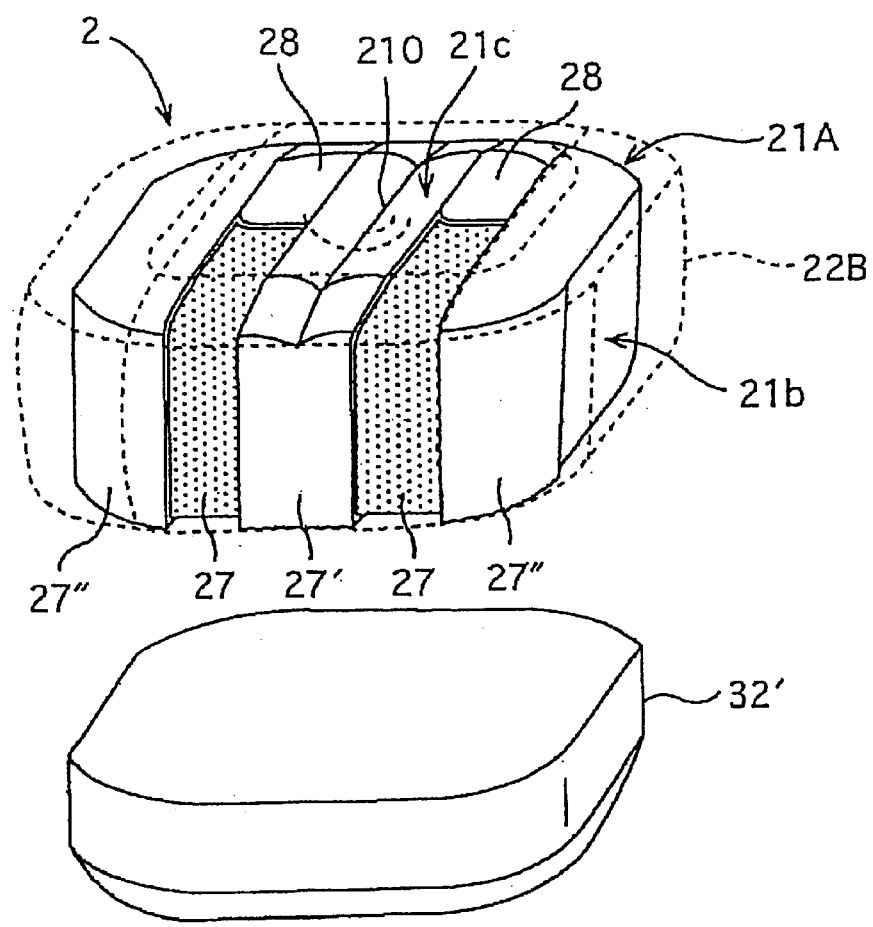
FIG. 19 is a perspective view to show the construction of the ninth example of the magnetic attachment.
Figure 20:
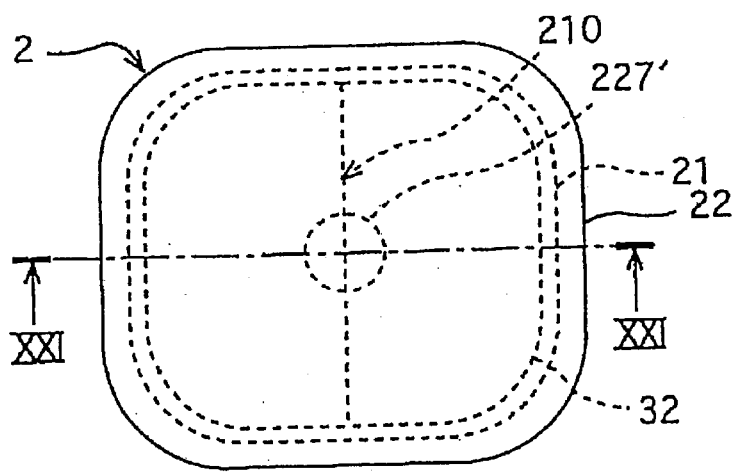
FIG. 20 is a ground plan to show the construction of the ninth example of the magnetic attachment.

The ninth example is very different from those above examples in point of the structure of the magnetic assembly 21A shown in FIG. 19. The structure changes from a circular to a rectangular in shape. As it is changed, the cap 22B is like a rectangular in shape which is not symmetrical with respect to the center axis as shown in FIG. 20. But the others of the cap 22B is same to the cap 22' of the sixth examples. In a similar situation the keeper 32' is like a rectangular in shape.

Figure 21:
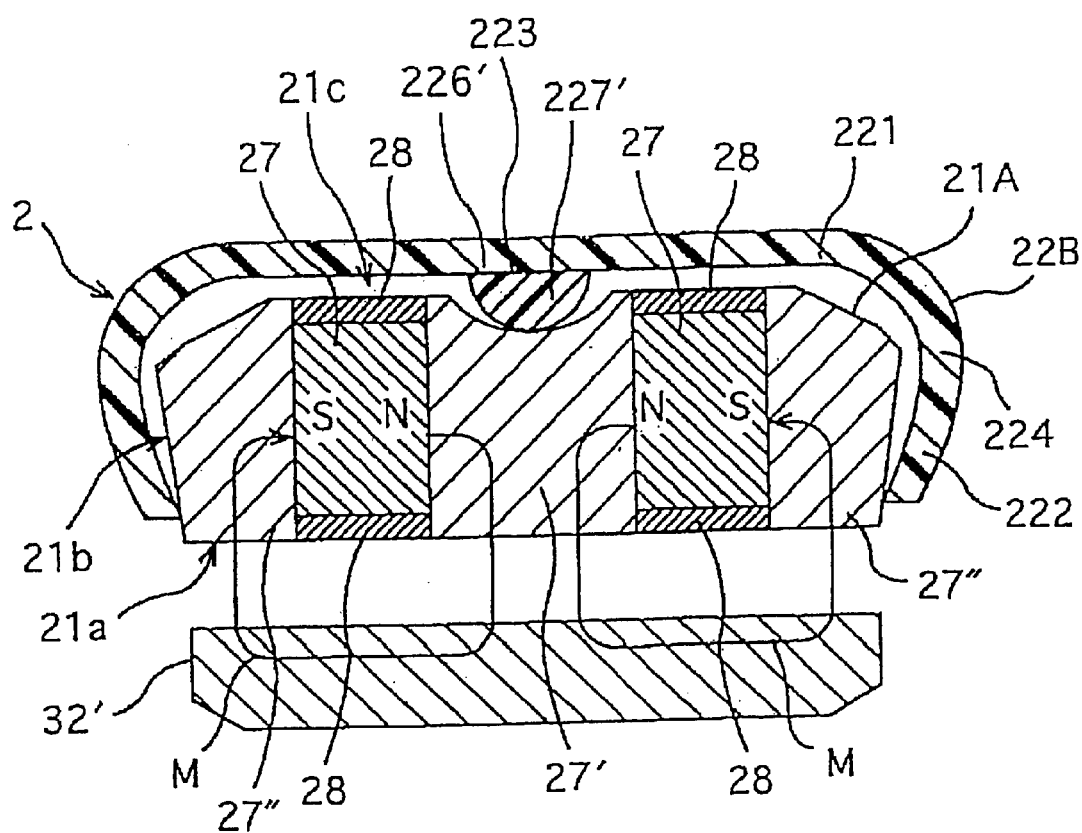
FIG. 21 is a cross section to show the construction of the ninth example of the magnetic attachment.
Figure 22:
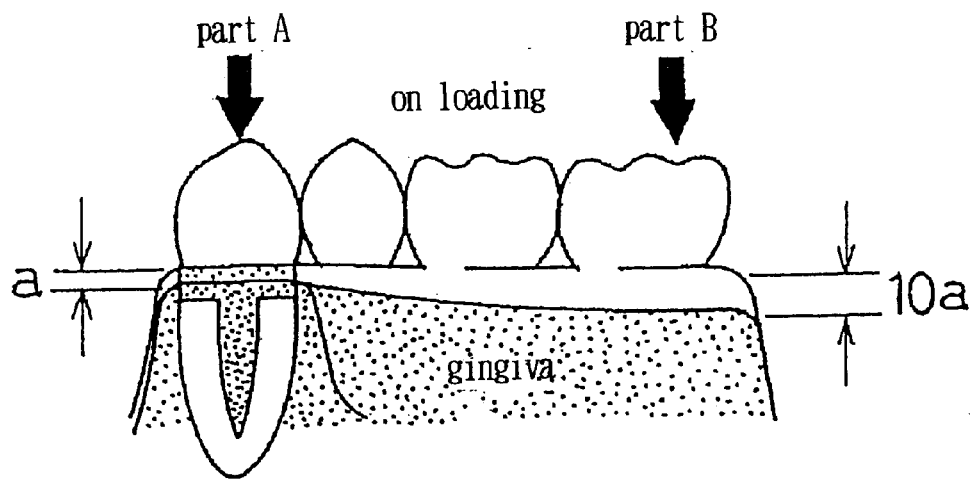
FIG. 22 is a diagram to illustrate the situation for the denture to set on the abutment teeth and sink on biting.
Figure 23:
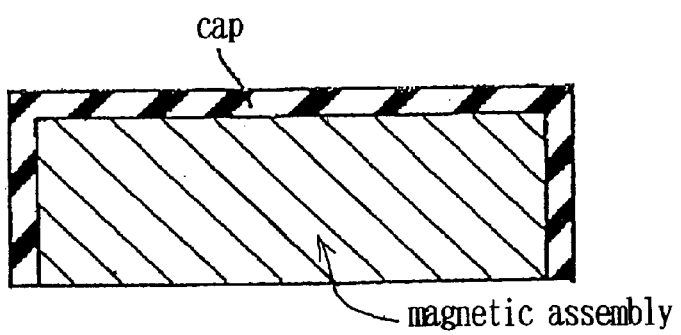
FIG. 23 is a cross section to show the construction of the previous magnetic attachment.
Figure 24:
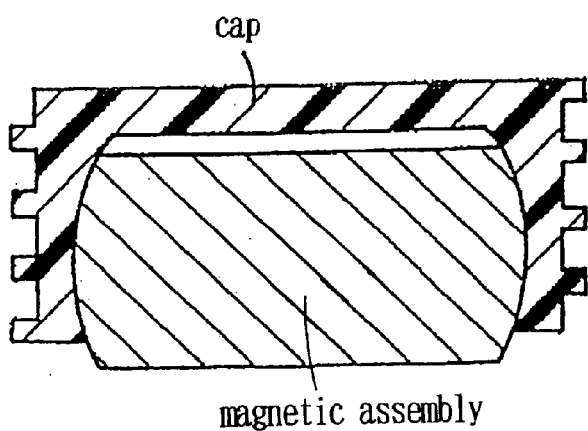
FIG. 24 is a cross section to show the construction of the previous magnetic attachment.

As shown in FIG. 21, the magnetic assembly 21A exhibits a double sandwich structure which consists of an intermediate block-shaped yoke 27', a seat shaped magnets 27 and an outer yokes 27" in turn from a center to both sides. The magnet is made of a rare earth magnet and these yokes are made of a soft magnetic stainless steel. The intermediate block-shaped yoke 27' is put between two seat shaped magnets 27 of which same poles, for example north poles, are faced each other. A set of the yoke 27' and two magnets 27 is put between two outer yokes 27", where the opposite face of two magnets 27 has same poles, for example south poles.

Similarly, it is seen from FIG. 21 that the magnetic assembly 21A makes a magnetic circuit with the keeper 32' so that a strong attractive magnetic force can be got.

For protecting magnets from corrosion, four faces of each magnet besides two contact faces with an intermediate yoke 27' and an outer yokes 27" is sealed by thin sealing cases 28 made of a non-magnetic stainless steel. Thin sealing cases 28 is laser-welded with both the intermediate yoke 27' and the outer yokes 27" so that two seat shaped magnets 27 is perfectly sealed. Here it is important to insulate the intermediate yoke 27' from the outer yokes 27" magnetically. So the thin sealing cases 28 are made of a non-magnetic stainless steel which prevents magnetic connection with them.

For making sure to join the cap 22B with the magnetic assembly 21A, the side 21b of the magnetic assembly 21A is tapered forward to the contact surface 21a.

The magnetic assembly 21' has a hollow 210 like a groove on the center of the top surface of the intermediate yoke 27. On the other hand a soft resin cushion button 227 of the cap 22 is contact with the bottom of the hollow in the condition that they are contact only at the center point of the bottom of the hollow 210. On non-loading as shown in FIG. 21, there remains a proper gap(S) between the top 21c of the magnetic assembly 21A and the core 221 of the cap 22B.

The present example has same cushion mechanics so as to offer the cushion property same to that of the seventh example. The present example is fixed to the denture base by a similar fixing method same to that of the first example which is previously described in details. But the spacer is different from that of the first example. That is, it is like a rectangular in shape to be fit to the shape of the magnetic assembly 21A. However the spacer has the effect same to that of the first example.

MODIFIED EXAMPLES

It is possible to design some modified structures of the ninth example which show triple or more sandwich structures having several magnets and intermediate yokes 27', where two magnets 27 which is faced each other has same poles. In this modified structure each magnet is so small as to bring only a little magnetic flux from it. These small magnetic circuits are made in same number to the number of the magnets. These small magnetic circuits make it possible to reduce the height of the magnetic assembly. The more are magnets, the thinner becomes the height of the magnetic assembly. This modified structure offers a special merit to reduce the height of the magnetic assembly.

ADVANTAGES OF THE PRESENT INVENTION

The present magnetic attachment having a cushion property gives a good solution as follows to the first object mentioned previously.

On biting, the denturel having the present magnetic attachment tends to sink uniformly on the abutment teeth for the cushion property. Uniformly sinking makes no concentration of the pressure on the abutment teeth. It means that the abutment teeth is kept to be in a good condition. This cushion property also restrains shaking of the denture 1 on the abutment teeth. And it also can lean the denture 1 on the abutment teeth keeping contact with the magnetic assembly and the keeper. That is, it offers a merit to hold the denture1 firmly in oral cavity due to the cushion property as well as the strong magnetic attractive force. Also a solution to the second object mentioned previously is made as follows. The fixing method of the present invention is useful for making sure to fix the magnetic attachment in the denture base by enough volume of self curing adhesive. Moreover the method offers another advantage to keep the space needed for the chusion property on biting without a considerable training.

What is claimed is:

1. A dental magnetic attachment for securing a denture in a patient's mouth by a magnetic attractive force, said dental magnetic attachment comprising:

a soft magnetic keeper for embedding in a top of a root cap, a magnetic assembly attracting the keeper by magnetic force, a cap covering the magnetic assembly, the cap including a top section at a designated distance over the top of the magnetic assembly with no applied load and moving towards the magnetic assembly upon loading, and including a circumferential section tightly fit to a circumferential edge of the magnetic assembly, the circumferential section sliding alone the circumferential edge of the magnetic assembly.

2. The dental magnetic attachment as set forth in claim 1, wherein the magnetic assembly has an indentation in a top surface and the cap has a protrusion fitting into the indentation of the magnetic assembly, the protrusion being compressible upon loading by a biting pressure.

3. The dental magnetic attachment as set forth in claim 2, wherein at least the protrusion of the cap is made of resin.

4. The dental magnetic attachment as set forth in claim 3, wherein the protrusion of the cap is made of resin, and the circumferential section of the cap is made of a corrosion resistant, non-magnetic material.

5. The dental magnetic attachment as set forth in claim 2, wherein the protrusion of the cap is made of soft resin, and a remainder of the cap is made of hard resin.

6. The dental magnetic attachment as set forth in claim 1, wherein elastic material entirely fills a space between the magnetic assembly and the cap.

7. The dental magnetic attachment as set forth in claim 1, wherein elastic material partially fills a space between the magnetic assembly and the cap.

8. The dental magnetic attachment as set forth in claim 1, wherein a lateral edge of the cap extends beyond a tip of the circumferential section.

9. The dental magnetic attachment as set forth in claim 1, wherein a lateral face of the magnetic attachment and an inner surface of the circumferential section of the cap are tapered outwardly.

10. The dental magnetic attachment as set forth in claim 1, wherein the magnetic assembly includes a ring-shaped magnet and a yoke, the yoke covering the ring-shaped magnet and filling a space in a center of the ring-shaped magnet to form a closed magnetic circuit when the magnetic assembly is paired with the keeper.

11. The dental magnetic attachment as set forth in claim 1, wherein the magnetic assembly includes a plurality of block-shaped magnets and a yoke filling spaces between the plurality of block-shaped magnets, the bock-shaped magnets are arranged with similar poles facing each other.

12. A method of fixing a dental magnetic attachment and a cap unit in a denture so as to prevent self-curing resin from entering a space beneath the cap unit, the space being necessary for movement of the cap unit with respect to the magnetic assembly upon loading, the method comprising:

placing a spacer between the cap unit and a root cap containing a keeper, the magnetic attachment and the cap unit being adhered to the root cap.

13. The method as set forth in claim 12, wherein the spacer is removed after curing of the self-curing resin.

14. The method as set forth in claim 12, wherein the spacer is placed underneath the cap unit during curing and the spacer is removed after completion of curing, the spacer preventing cured resin from restricting movement of the cap unit.

15. The method as set forth in claim 14, wherein the spacer has a ring shape to be placed beneath the cap unit and the magnetic assembly.

* * * * *